United States Patent [19]
Langford

[11] Patent Number: 5,441,622
[45] Date of Patent: Aug. 15, 1995

[54] SHARPS DESTRUCTION APPARATUS

[75] Inventor: Terrence R. Langford, Tucson, Ariz.

[73] Assignee: KEW Import/Export, Inc., Tucson, Ariz.

[21] Appl. No.: 48,276

[22] Filed: Apr. 14, 1993

Related U.S. Application Data

[63] Continuation-in-part of Ser. No. 957,722, Oct. 6, 1992, Pat. No. 5,277,868.

[51] Int. Cl.$^6$ .............. C25C 7/00; A61L 2/00; A61L 2/02
[52] U.S. Cl. ............... 204/275; 204/140; 204/155; 204/242; 204/297 M; 422/21
[58] Field of Search ......... 204/275, 297 M, 155, 204/140, 141.5, 144, 146, 242

[56] References Cited

U.S. PATENT DOCUMENTS

| | | | |
|---|---|---|---|
| 1,420,127 | 6/1922 | Moxham | 204/297 M |
| 1,873,826 | 8/1932 | Deveus | 204/297 M |
| 2,043,823 | 6/1936 | Young | |
| 2,890,992 | 6/1959 | Hoehl | 204/297 M |
| 3,268,428 | 8/1966 | Buccino | 204/297 M |
| 3,421,989 | 1/1969 | Haagen-Smit | 204/413 |
| 3,445,364 | 5/1969 | Strickler | 204/405 |
| 3,901,786 | 8/1975 | Wheelwright et al. | 204/225 |
| 4,318,786 | 4/1982 | Lahoda et al. | 204/141.5 |
| 4,385,972 | 5/1983 | Vanderpool | 204/146 |
| 4,391,694 | 7/1983 | Runsten | 204/275 |
| 4,452,358 | 6/1984 | Simpson | 206/366 |
| 4,627,893 | 12/1986 | Cormier et al. | 204/401 |
| 4,710,233 | 12/1987 | Hohmann et al. | 134/1 |
| 4,909,995 | 4/1990 | Jacob | 422/186.29 |
| 5,138,125 | 8/1992 | Salesses | 219/68 |
| 5,166,488 | 11/1992 | Peppard | 219/10.55 R |

FOREIGN PATENT DOCUMENTS

546465  3/1932 Germany.
424246 11/1993 United Kingdom.

Primary Examiner—T. Tung
Attorney, Agent, or Firm—Ogram & Teplitz

[57] ABSTRACT

A hygienic apparatus which totally dissolves sharps from such places as health-care centers, operating rooms laboratories, and the like. The apparatus accepts all sorts of metal sharp instruments. The sharp metal portion is removed from any plastic component of the instrument. The plastic components are collected for sterilization through microwaves or similar process; the sharp metal instruments are dissolved using electrolysis and the liquid is discharged into conventional sewer systems. The sharp instruments, until their dissolution, are secured by a magnet within the apparatus.

44 Claims, 5 Drawing Sheets

SHARPS DESTRUCTION APPARATUS

This is a continuation-in-part of U.S. patent application Ser. No. 07/957,722, entitled "Syringe Destruction Device" and filed Oct. 10, 1992, now U.S. Pat. No. 5,277,868.

BACKGROUND OF INVENTION

This invention relates generally to medical waste disposal and more specifically to the sterilization and disposal of contaminated syringes.

Syringes are commonly used in many environments including hospitals, doctors offices, dentists offices, and even at home by diabetics or others who require at-home hypodermic injections. The typical syringe consists of a hollow steel needle threadably coupled to a plastic barrel. A plastic plunger with a rubber gasket is inserted into the barrel for forcing fluids into and out of the plastic barrel and needle. Syringes are used to inject fluids into a body and to remove fluids from a body.

Syringes have always posed health and safety dangers. The sharp needles can stab a person accidentally, even when they are using the utmost care. The contaminated syringes can infect personnel through a needle wound or from spillage of their contaminated contents.

Today, however, the need for safe disposal of syringes is more important than ever. Serious and deadly diseases such as Acquired Immune Deficiency Syndrome (A.I.D.S.) and hepatitis can be transmitted by a single needle injury. Often it is not known whether a patient is infected with a serious disease, thus causing fear and concern about all syringes.

The needle portion of a syringe poses two health and safety dangers. First, the needles are sharp and can cause a severe injury. When disposed of, the needles can puncture a waste container or bag and injure unsuspecting personnel. Waste disposal personnel can be injured by needles protruding from plastic garbage bags or from other inadequate waste disposal containers. Even after disposal, sharp needles poses a danger since they have been known to wash up on beaches or turn up in other public places.

Second, needles can pass on diseases, many of them very serious. Many diseases are highly infectious and contagious. A single needle prick from a contaminated needle can infect a person with one of these diseases. Some infectious diseases can be passed to personnel without even a needle prick, mere contact with the needle may be enough. The needles pose a health and safety threat until they have been completely neutralized by sterilization and by disabling the sharp portions.

Syringes pose a health and safety threat even after the needle has been removed. The barrel/plunger portion of the syringe often contains fluids contaminated with infectious diseases. The contaminated fluid in the barrel/plunger portion can leak or spill, thus spreading the disease. This can cause infection of medical personnel, patients, waste disposal personnel and others who come in contact with this waste. After final disposal of the syringe, the contaminated fluids can leak into the ground and contaminate ground water. The barrel/plunger portion of syringes pose a health and safety threat until they have been completely sterilized.

Many devices for disposal of syringes are known. However, they are all lacking in one or more ways.

U.S. Pat. No. 5,003,892 issued to Bricken on Apr. 2, 1991 discloses a process for the sterile disposal of syringes. The Bricken process places used syringes into a container and heats the syringes until the melted plastic encapsulates the needles thus sterilizing and neutralizing the needles at the same time. This process, however, is not practical for disposal of syringes one at a time. It does not prevent spillage of infectious material when syringes are placed into the container nor does it provide for disassembly and sterilization of parts contaminated by such spillage. Finally, it does not provide a means for collecting noxious fumes produced from the process.

U.S. Pat. No. 5,106,594 issued to Held et al. on Apr. 21, 1992 shows an apparatus and method for disintegrating a wide variety of medical wastes and disinfecting them with radio waves. The large scale and complexity of this device restricts its use to large bulk processing of medical wastes. Also, waste products remain in their infectious and dangerous state while waiting for processing.

U.S. Pat. No. 4,900,500 issued to Honeycutt on Feb. 13, 1990 teaches a process of sterilizing and immobilizing potentially infectious devices by means of enveloping them within a hardening polymer that thermally sterilizes the contents by means of an exothermic polymerization reaction. This is essentially bulk processing and requires storage of hazardous waste while enough waste for a batch is accumulated. The process is time consuming, odor causing, and the enclosing polymer will ultimately decompose.

There are numerous other U.S. patents for syringe disposal devices. Most are lacking in one or more respects. Many do not sterilize the infectious waste, others do not disable the sharp needles, still others only process wastes in bulk. Finally, some are complicated, dangerous to use, or give off noxious odors.

Clearly, there exits a need for an improved syringe disposal device which is on-site, simple to use, processes single syringes, provides immediate sterilization, and disables the sharp needles.

SUMMARY OF INVENTION

The invention creates a hygienic apparatus which totally dissolves sharps from such places as health-care centers, operating rooms, laboratories, and the like. The apparatus accepts all sorts of metal sharp instruments. The sharp metal portion is removed from any plastic component of the instrument. The plastic components are collected for sterilization through microwaves or similar process; the sharp metal instruments are dissolved using electrolysis and the liquid is discharged into conventional sewer systems. The sharp instruments, until their dissolution, are secured by a magnet within the apparatus.

In one embodiment of the invention, the apparatus creates a simple to use, single quantity, syringe sterilization and destruction device. The device heats the steel needle portion of a syringe to sterilize the needle portion. The heat melts the steel-to-plastic fitting between the steel needle portion and the plastic barrel portion of the syringe. The barrel portion separates from the needle portion of the syringe by force of gravity or by a light pulling force exerted by a pulling mechanism. The hole in the fitting is sealed by the molten plastic. Sealing the hole maintains the integrity of the barrel/plunger container and prevents spillage of contaminated waste. The heated needle is bent into a spiral bundle so that no sharp portions protrude from the spiral bundle. The spiral bundle is deposited into a container for recycling or disposal. The barrel/plunger portion is placed into a microwave oven and heated until sterile.

In an alternate embodiment the barrel/plunger portion is heated in the microwave oven until the plastic barrel/plunger portion is melted.

The needles and barrel/plungers are now sterile and safe. Both the needle and barrel/plunger waste can be disposed of safely or recycled.

The device is simple to use, can process single syringes, and is small enough for use in a small medical office, at home, or anywhere syringes are used.

The first step in using the device is to insert the syringe into the device. The syringe is inserted into the device needle first. The preferred embodiment provides a loader tray to hold the syringe, aid the user in inserting the syringe into the device, and to catch any spillage of contaminated waste. The device grips and holds the syringe and activates the sterilization and needle disabling process.

In the preferred embodiment, the gripping means holds the syringe at the base of the needle portion where the plastic barrel portion and needle portion are attached.

The needle portion is heated to sterilize the needle and to assist the separation of the needle from the barrel portion of the needle. The preferred embodiment uses simple induction heating to heat the needle. The needle is heated to a sufficient temperature and for a sufficient time to completely sterilize the needle. As the needle is heated above the melting point of the plastic barrel portion, the plastic barrel portion separates from the needle portion and drops into the loader tray.

When the plastic barrel separates from the needle, the hole created in the plastic barrel is conveniently sealed by the molten plastic. This seals the barrel/plunger assembly thus preventing spills and leaks of contaminated waste.

The sterilized needle is then bent to disable the sharp portion of the needle. The preferred embodiment rolls the needle into a spiral bundle with the sharp end of the needle at the center of the bundle and the threaded end pressed flat against the spiral bundle. Those of ordinary skill in the art readily see other bending configurations that achieve the objective of disabling the sharp portion of the needle.

The sterilized needle bundle is dropped into a container where it is safely stored until disposal or recycling. The needle in completely safe at this time since it has been sterilized and the sharp portion has been disabled.

In one embodiment of the invention, the sharp (the hypodermic needle in this example) is merely withdrawn from the plastic barrel/plunger and the sharp needle is dropped into an electrolytic bath which disintegrates the metal into a liquid sludge. This sludge is sterilized through ozone or a detergent/germicide combination and then flushed into the sewer drain.

Note in this embodiment, no solid metal product is left whatsoever. Only a metallic salt sludge remains which is completely harmless and sterilized/disinfected. Without solid metal parts, there doesn't exist any potential for pricks or cuts from the hypodermic needle.

This same embodiment is also used for the destruction of scalpels (both disposable and reusable scalpels). The blade of a scalpel is removed and dropped into the electrolytic solution via an opening in the device and the entire scalpel blade is rendered a liquid sludge. In the case where the entire scalpel is metallic and all of it is to be destroyed, the entire assembly is dropped into the electrolytic solution.

For a disposable plastic handle scalpel, just as with the syringe, the metal portion (the blade for a scalpel) is inserted into a slot which heats the metal and withdraws the metal from the handle; the metal blade falls into the electrolytic solution. The plastic handle falls into another container for separate sterilization and disposal.

In like manner, a reusable scalpel has its blade removed via slotted key approach which then drops the metal blade into the electrolytic solution for dissolution. The reusable metal handle is dropped into another container for washing and/or sterilization.

Within the electrolytic solution, the solid metal is restrained from the liquid sludge through a use of a magnet which holds the solid metals proximate to the anode for proper dissolution. In this manner, the operator is assured that by flushing of the sludge, sharp solid metal pieces are not also discharged.

Another function of the magnet is to provide a rhythmic motion to the metallic objects. This is accomplished by a mechanism in the magnet mount which moves the magnet(s). The rhythmic motion maintains a fresh metallic surface exposed to the electrolytic solution.

One method of disposing of the plastic components calls for the plastic barrel/plunger portion being dropped into a microwave oven. The preferred embodiment provides a container to hold the barrel/plungers in the center portion of the microwave oven. This eliminates the chance of a barrel/plunger falling into a "shadow" area of the oven where the microwave energy is less intense and enhances the effectiveness of the microwave sterilization.

The operator closes the door and turns on the microwave oven. The oven operates at a sufficient power level and for a sufficient time to sterilize the barrel/plungers and any waste contained inside them. In an alternate embodiment, the barrel/plungers area heated until they are melted, creating a block of sterilized plastic.

When the process is completed, the syringe is sterilized and the needle is disabled. The steel needles and plastic barrel/plungers are no longer hazardous wastes and can be disposed of as normal waste or recycled.

DETAILED DESCRIPTION OF THE DRAWINGS

Figure 1:
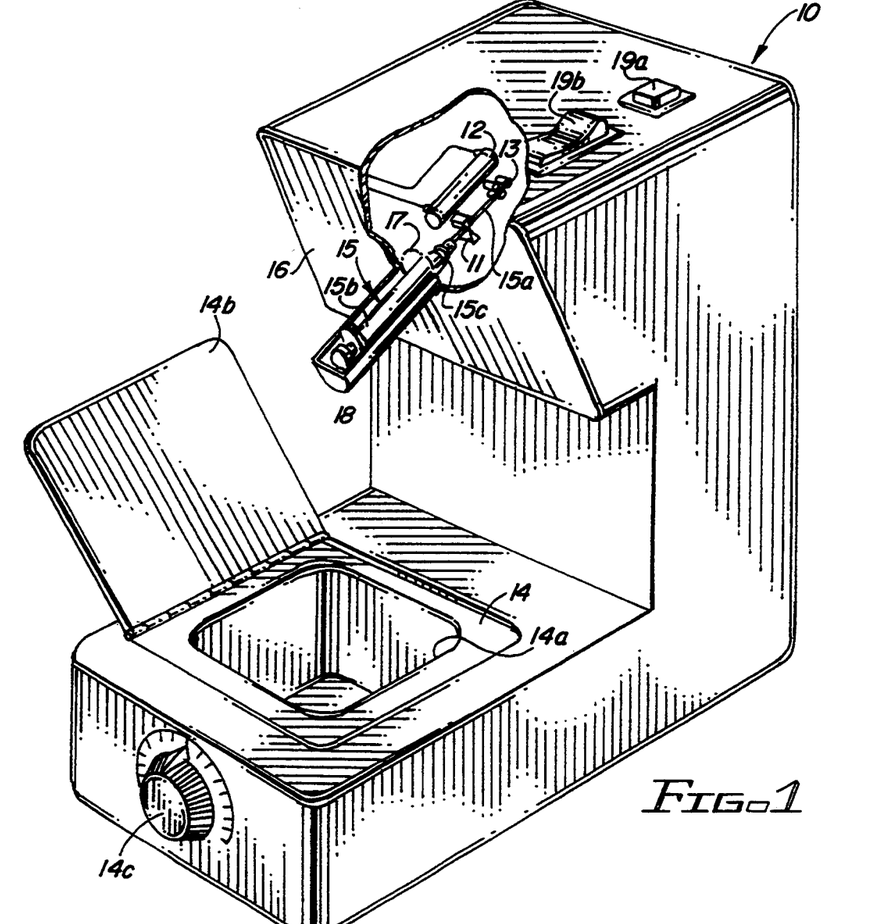
FIG. 1 is a perspective view of the preferred embodiment of the invention.

FIG. 1 is a perspective view of the preferred embodiment of the invention.

The housing 10 encloses the needle gripping means 11, heater 12, needle bending means 13, and microwave oven 14.

The contaminated syringe 15 is inserted into the device 16 through opening 17. The syringe 15 is inserted needle first. The insertion is aided by loader tray 18. The loader tray 18 precludes operator error during insertion and catches any spillage of contaminated waste when the syringe 15 in inserted into the device 16.

In the preferred embodiment, syringe 15 is inserted at a slightly upward angle so the barrel/plunger portion 15b is lower than the needle 15a. This angle aids in the separation of the barrel 15b from the needle 15a as described below.

Insertion of syringe 15 actives gripping means 11 which hold the syringe 15 in the device 16. Those of ordinary skill in the art readily see various embodiments of gripping means to hold a needle.

The heater 12 begins heating the steel needle 15a. The preferred embodiment uses low frequency electromagnetic induction heating to heat the needle 15a. Those of ordinary skill in the art readily see alternate methods that can be employed to heat the needle 15a. These include, but are not limited to, high frequency induction heating, electric radiant heat, gas flame, microwave radiation, and radio waves.

Heater 12 heats needle 15a to a sufficient temperature and for a sufficient time to completely sterilize the needle 15a. Heater 12 also heats the needle 15a to a sufficient temperature to melt the plastic fitting 15c between the barrel 15b and the needle 15a. As the plastic fitting 15c melts, gravity pulls the barrel 15b from the needle 15a. When barrel 15b separates from needle 15a, barrel 15b and plunger 15d drop into loader tray 18.

The hole created by the separation of barrel 15b and needle 15a is sealed by the molten plastic. Sealing the barrel 15b and plunger 15d assembly serves the dual purpose of preventing spillage and providing a secondary sealed container for the enclosed contaminated waste.

In an alternate embodiment, the loader tray 18 is not used, thus allowing the barrel 15b and plunger 15d to fall directly into the microwave oven 14.

The sterilized needle 15a is bent by bending means 13 to disable the sharp portion of the needle 15a. The preferred embodiment bends the needle 15a into a flat spiral bundle. The sharp portion of the needle 15a is in the center of the bundle and therefore rendered harmless. The bending process is accomplished with a simple gripping/bending device 13. The gripping/bending device grabs the sharp portion of the needle 15a and rolls the needle 15a into a spiral. The threaded end of the needle 15a is pressed flat against the spiral bundle to further eliminate any sharp edges. Those of ordinary skill in the art readily see other bending configurations and other bending devices which accomplish similar results.

When the sterilization and bending processes are complete, the needle bundle is dropped into a needle container (not shown) for storage until it can be disposed of.

The still contaminated barrel 15b and plunger 15d are in the loader tray 18. The loader tray 18 is removed from the device 16 and the barrel 15b and plunger 15d are dropped into the microwave oven 14. Loader tray 18 is readily washable and is ordinarily not contaminated since the needle is laid on the loader tray 18 with its tip upward.

The preferred embodiment provides a microwaveable container 14a to hold the barrels 15b and plungers 15d in the microwave oven 14. The container 14a holds the barrel/plungers 15b in the center portion of the microwave oven 14. This prevents a barrel 15b and plunger 15d assemblies from dropping into a corner of the microwave oven where there may be "shadows" and the microwave energy may be less intense.

The barrel 15b and plunger 15d are sterilized by microwaves from microwave oven 14. The operator closes oven door 14b and turns on the microwave oven 14 via timer 14c. In the preferred embodiment, microwave oven 14 heats the barrel 15b and plunger 15d to a sufficient temperature and for a sufficient time to sterilize the barrel 15b and plunger 15d.

The microwave oven 14 can be cycled after each syringe is disposed of, or the operator can wait until several barrels 15b and plungers 15d need to be sterilize.

In an alternate embodiment, the barrel 15b and plunger 15d are heated to a temperature sufficient to melt the plastic. This creates a sterile block of plastic which is ready for disposal or recycling.

Those of ordinary skill in the art can readily see that other similar sterilization means may be employed to achieve the sterilization. These include, but are not limited to, electromagnetic fields, radio frequency waves, and the like.

Switch 19a controls power to device 16. Light 19b indicates when power is being supplied to device 16.

Figure 2:
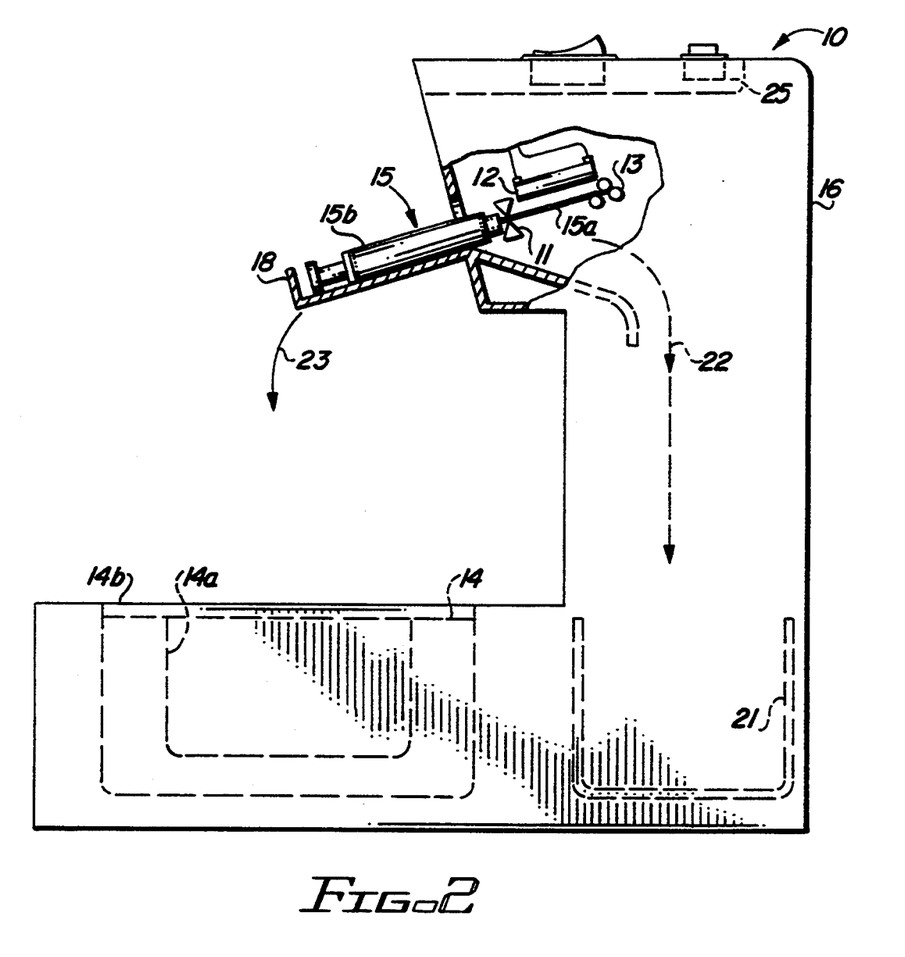
FIG. 2 is a side view of the preferred embodiment of the invention.

FIG. 2 is a side view of the preferred embodiment of the invention.

Syringe 15 is placed into loader tray 18. Loader tray 18 aids the user in inserting syringe 15 into the device 16. Tray 18 precludes operator error and catches any accidental spillage upon introduction of syringe 15 into the device 16. Loader tray 18 is removable for easy cleaning.

Needle 15a is held by gripping means 11. Heater 12 heats needle 15a to a sufficient temperature and for a sufficient time to sterilize needle 15a and to melt the plastic fitting between needle 15a and plastic barrel 15b.

The small effusion of vapor from the heating process is absorbed by canister 25. Canister 25 contains activated charcoal or a similar substance to absorb the vapors. Canister 25 is removable for periodic replacement.

By the force of gravity, plastic barrel 15b separates from needle 15a when the fitting 15c is sufficiently melted. As the separation occurs, the molten plastic seals the hole left by the removal of needle 15a.

The bending means 13 bends the needle 15a such that the sharp portion of the needle 15a is disabled. The preferred embodiment rolls the needle 15a into a flat spiral with the sharp portion at the center and the threaded end pressed flat against the spiral bundle. After the bending operation, needle 15a is safe for disposal. The needle 15a is sterile and has no sharp portions. The spiral needle bundle is dropped into a container 21, as shown by arrows 22, for temporary storage.

The barrel portion 15b is resting in the loader tray 18 after separation from the needle 15a. The operator removes the loader tray 18 from the device 16 and dumps the barrel 15b and plunger 15d into the microwave oven 14.

In an alternate embodiment, the loader tray 18 is not used. The syringe 15 is placed directly into the device 16. When the barrel 15b separates from the needle 15a, the barrel 15b and plunger 15d drop directly into the microwave oven as shown by arrow 23.

A container 14a is located inside the microwave oven 14 to receive the barrel 15b and plunger 15d. Container 14a holds the barrel 15b and plunger 15d in the center portion of the microwave oven 14. This assures that the barrel 15b and plunger 15d do not fall into a corner of the microwave oven 14 and that they are fully exposed to the microwaves (not shown).

Figure 3:
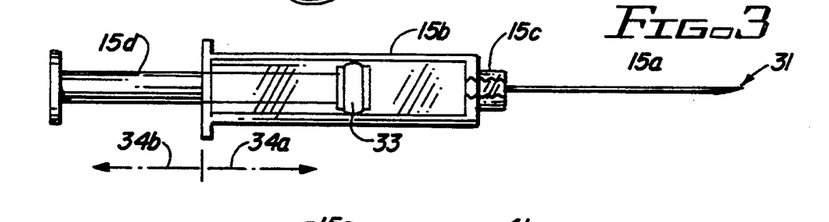
FIG. 3 is a side view of a syringe.

FIG. 3 is a side view of a typical syringe.

Figure 4A:
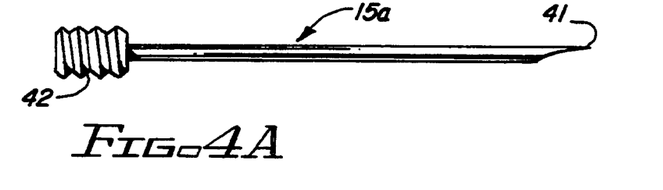
FIG. 4a is a needle portion of a syringe.

The hollow steel needle portion 15a is threadably attached to the plastic barrel 15b via fitting 15c. The sharp portion is in indicated by arrow 31. Plunger 15d extends into the interior of barrel 15b. Plunger 15d has a rubber gasket 33 to create a seal against the interior of barrel 15b. Plunger 15d is moveable by an operator as shown by arrows 34a and 34b. Actuation of plunger 15d, as shown by arrow 34a, propels fluid from the interior of barrel 15b, through the hollow steal needle 15a and out the sharp portion of the needle 15a. FIG. 4a shows a needle portion of a syringe before it is bent. The sharp portion 41 is dangerous and must be disabled. The threaded portion 42 may also have sharp edges and also must be disabled.

Figure 4B:
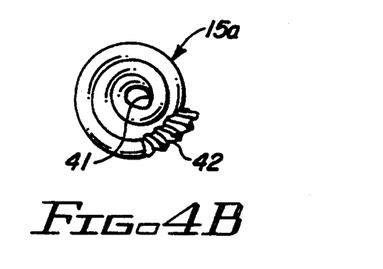
FIG. 4b is a needle portion of a syringe after it is bent into a spiral bundle by the invention.

FIG. 4b shows a needle portion of a syringe after it is bent into a flat spiral bundle.

This figure shows the preferred bending configuration. Needle 15a is bent into a flat spiral. The sharp portion 41 is at the center of the spiral. The sharp portion 41 does not protrude from the bundle and is safe. The threaded portion 42 is pressed tightly against the periphery of the spiral bundle to further eliminate any sharp edges.

Figure 5A:
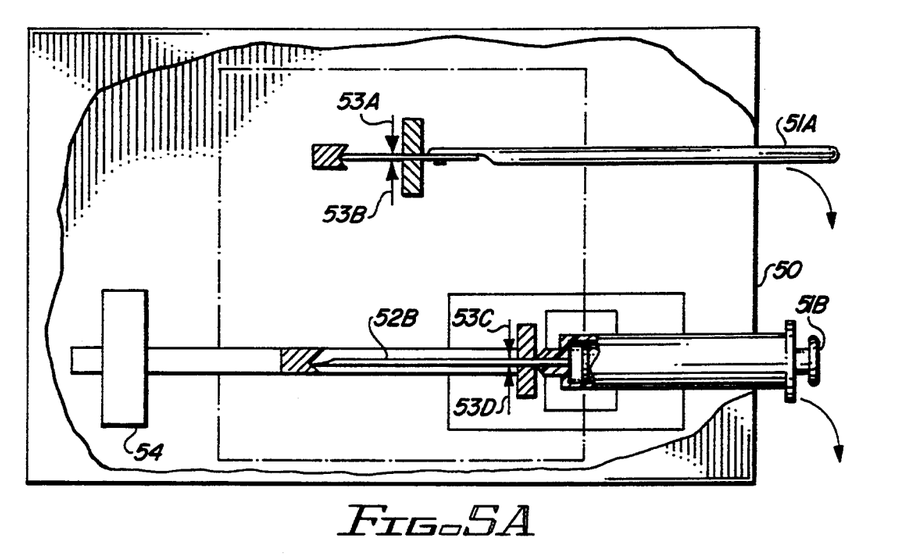
FIGS. 5A and 5B are top and side views respectively of an embodiment of the invention which utilizes an electrolytic solution for the destruction of sharps.
Figure 5B:
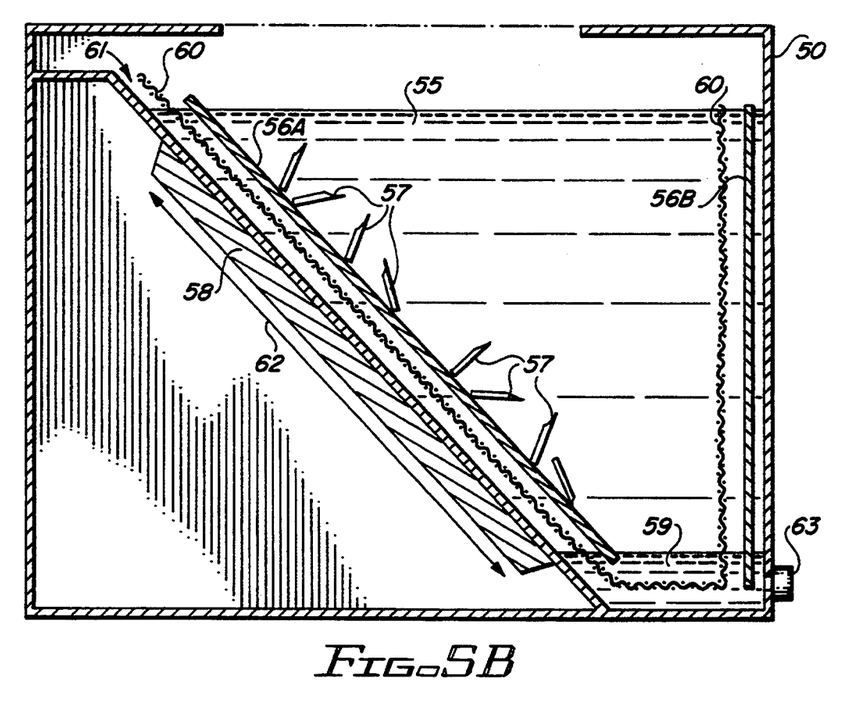

FIGS. 5A and 5B are top and side views respectively of an embodiment of the invention which utilizes an electrolytic solution for the destruction of sharps.

FIG. 5A is the top view of the sharps destruct mechanism which is contained within housing 50. In the case of a plastic syringe 51B, the hypodermic needle 52B is inserted through a hole which causes contact with the electrical contacts causing heating elements 53C and 53D to activate and heat the metal portion of the hypodermic needle 52B. Heating element 53D is located proximate to the plastic barrel of syringe 51B; heat therefrom causes slight melting of the plastic permitting puller 54 to grasp and withdraw hypodermic needle 52B from the plastic barrel.

The hypodermic needle is permitted to fall into the destruct chamber, the plastic barrel falls into a collection basket (not shown).

In similar manner, when scalpel 51A is inserted into a slot, metal blade 52A contacts the electrical contacts and causes heating elements 53A and 53B to heat the metal blade 52A. Heating element 53B is located proximate to the handle portion and is used to release the metal blade 52A from the plastic handle portion of a disposable scalpel. The plastic handle, as with the plastic barrel of the syringe, falls into a collection basket (not shown).

Should a reusable scalpel be used, the blade is secured within the slot permitting the operator to twist the handle and release the blade for destruction.

The destruction portion of the invention is shown in FIG. 5B.

The metal components fall into tub 61 which contains an electrolytic solution 55. The sharps 57, drawn by magnet 58, collect against anode 56A. In this manner, sharps 57 are restrained until they are finally dissolved into a liquid sludge 59.

This dissolution is accomplished by passing an electrical current between the anode 56A and cathode 56B. By oscillating the magnet 62, the sharps 57 are moved to maintain fresh metallic exposure to the electrolyte so that optimal dissolution occurs.

Basket 60 is used to remove undissolved sharps and the anode when it is time to replace the anode with a fresh one.

Periodically, the solution is sanitized through the introduction of ozone, as discussed previously, or by the addition of a detergent/germicide mixture. Those of ordinary skill in the art readily recognize various other sanitizing and sterilizing techniques which can be used in this context.

The sludge 59 and the eletrolytic solution 55 is passed into the sewer system via ports 63. Without any solid components, the sludge poses no risk of cutting or puncturing and are easily and safely discarded in this manner.

Figure 6:
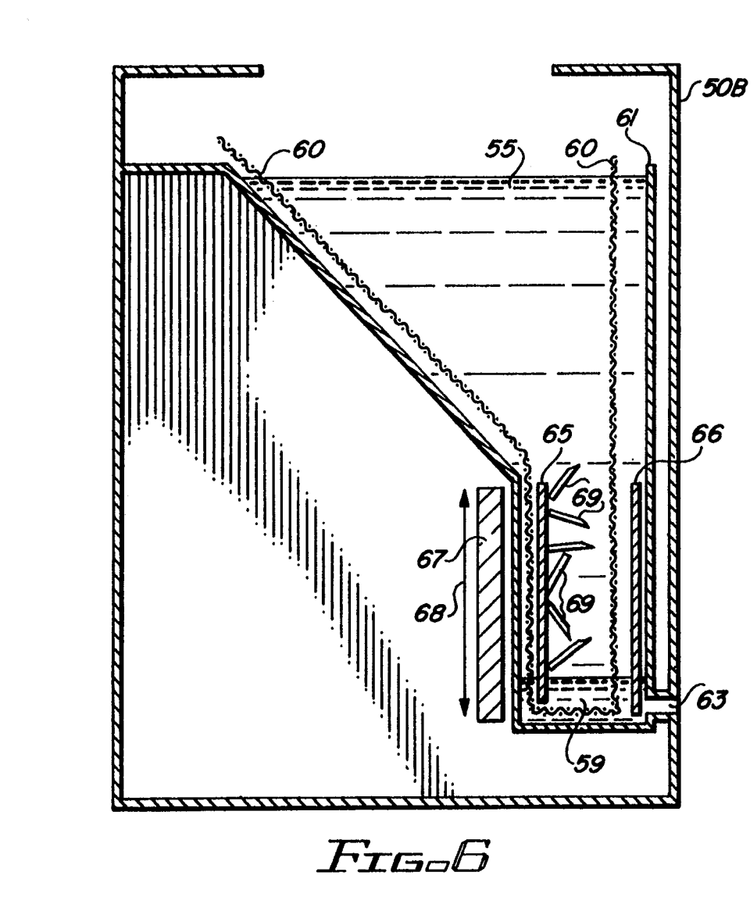
FIG. 6 is a side view of the preferred electrolytic destruct apparatus.

FIG. 6 is a side view of the preferred electrolytic destruct apparatus. As with the destruct device discussed relative to FIGS. 5A and 5B, the eletrolytic solution 55 is contained within tube 61 with screen 60 interposed therein.

In this preferred embodiment, the anode 65 and cathode 66 are positioned to be parallel to each other. As with the other embodiments, magnet 67 is used to secure the sharps 69 against the anode 65. Slight oscillations of magnet 68, cause the sharps 69 to dissolve and settle as sludge 59.

Figure 7:
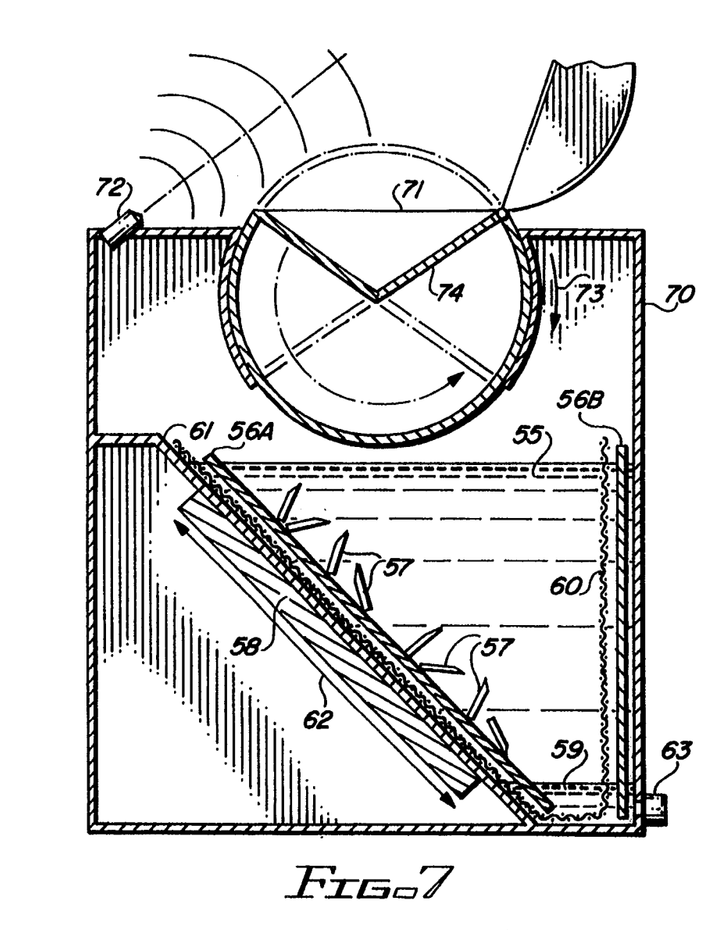
FIG. 7 is a side view of an embodiment of the electrolytic destruct apparatus utilizing an automatic box which deposits the sharps into the electrolytic bath.

FIG. 7 is a side view of an embodiment of the electrolytic destruct apparatus utilizing an automatic box which deposits the sharps into the electrolytic bath.

This embodiment utilizes a revolving catch 71 which accepts the placement of the sharps into a catch basin 74. This basin secures the sharps until the catch rotates, as indicated by arrow 73, to drop the sharps into electrolytic solution 55.

Catch 71 is activated through the use of a proximity sensor 72 which determines when an operator or other item is positioned to drop something into catch basin 74.

Once the sharps is deposited into electrolytic solution 55, the same process as discussed before occurs, that is the sharps 57 are drawn to the anode 56A through magnet 58. Current passing between the cathode 56B and anode 56A dissolves the metal sharps and renders them into sludge 59 which is flushed into the sewer via port 63.

This embodiment provides for an improved depositing mechanism since the operator need never come in actual contact with the destruction mechanism 70 due to the automatic opening and closing of the catch 71.

Figures 8, 9, 10A, 10B:
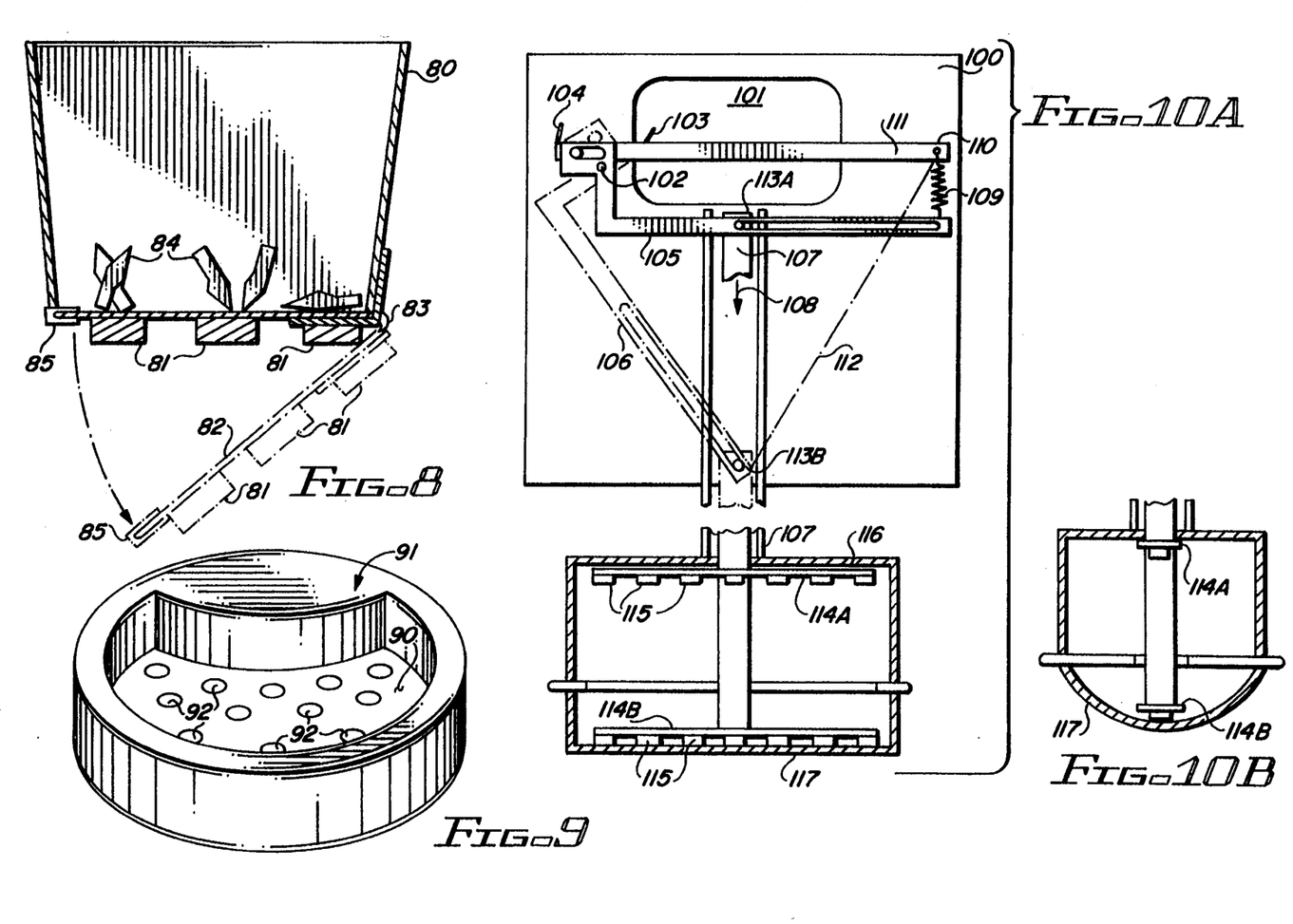
FIG. 8 is a side view of a container used for securing the sharps before their deposit into the sharps destruct apparatus.
FIG. 9 is a perspective view of an apparatus used to keep track of used needles within a surgical setting.
FIGS. 10A and 10B are functional diagrams of a sharps pick-up device from the front and side views.

FIG. 8 is a side view of a container used for securing the sharps before their deposit into the sharps destruct apparatus.

This device even further assists in the collection and depositing of the sharps. In this embodiment, surgical needles are dropped into metal basin 80 which is rubber coated in the preferred embodiment (not shown here). The needles are kept in basin 80 via magnet 81 which causes the magnetic field to pass throughout basin 80 and secure sharps 84. The magnet arm is secured to contact the bottom of basin 80 via releasable catch 85.

When the operator wishes to drop the surgical needles from the basin, releasable catch 85 is released and magnet 81 is swiveled via hinge 83 to position 82; thereby releasing the magnetic field from basin 80.

This mechanism is particularly useful for use with the embodiment of the destruct mechanism illustrated in FIG. 7 since the presence of basin 80 causes the catch to open and then the operator deposits the needles by moving magnet 81.

FIG. 9 is a perspective view of an embodiment used to maintain count of the needles used in a surgical theater.

Basin 90 has recessed area 91 in which a plurality of individual magnets 92 are embedded. As a surgical needle is used, it is placed on a specific numbered magnet (numbers not shown) so that proper count of the needles is maintained.

FIGS. 10A and 10B are functional diagrams of a sharps pick-up device from the front and side views.

The top portion of the sharps pick-up device has handle portion 100 with opening 101 therein. The operator is able to grasp activation bar 103 through opening 101 and by squeezing the activation bar 103, cause the device to become operation. Squeezing of the activation bar 103 causes pressure bar 105 to rotate around fixed pin 102 to the position shown by 106. This rotation causes pressure bar 105 to press push bar 107 from position 113A to position 113B. Spring 112 contracts to position 109 when the operator releases activation bar 103.

As activation bar 107 moves downward, magnetic bar 116 having magnets 115 attached thereto, is pressed from position 114A to position 114B. In this position, magnets 115 are in contact with the base member permitting the magnetic field to extend past the base member and adhere to metal sharps which lie on the floor.

A side view of the bottom portion is illustrated in FIG. 10B.

Base plate 117 is a curved member permitting the sweeper to be moved easily across the floor and thereby collect the metal sharps when magnet bar 114B is in contact with base plate 117. When the operator wishes to dislodge the metal sharps, release of handle 111 causes magnetic bar 114A to rise and remove the magnetic field holding the metal sharps.

It is clear from the foregoing that the present invention represents a new and useful apparatus for the sterile and safe destruction of syringes and scalpels at the point of use.

What is claimed is:
1. A sharps destruct apparatus comprising:
a) a chamber for receipt of said sharps;
b) an electrolytic solution contained in said chamber;
c) an anode positioned along an interior portion of a first wall of said chamber;
d) a cathode positioned along an interior portion of a second wall of said chamber;
e) a magnet positioned along an exterior portion of said first wall;
f) means for supplying electrical current between said anode and said cathode via said electrolytic solution such that said sharps are dissolved into said electrolytic solution;

g) an opening for receipt of said sharps;
h) means for withdrawing said sharps from a handle portion when said sharps are inserted through said opening;
i) means for depositing removed sharps in said chamber; and,
j) a means for discharging sludge containing said electrolytic solution and said dissolved sharps.

2. The sharps destruct apparatus according to claim 1 further including: a top member for enclosing said chamber.

3. The sharps destruct apparatus according to claim 2 wherein said opening includes a door mechanism means for covering said opening when said apparatus is not in use.

4. The sharps destruct apparatus according to claim 3 further including a proximity sensor for opening said door mechanism means when an object is within a selected zone of said door mechanism means.

5. The sharps destruct apparatus according to claim 4 further including a container means for holding said sharps prior to introduction into said opening.

6. The sharps destruct apparatus according to claim 5 wherein said container means include:
a) a metal bowl; and,
b) a magnet attached to an exterior portion of said metal bowl.

7. The sharps destruct apparatus according to claim 6 further including a rubberized lining on an interior surface of said metal bowl.

8. The sharps destruct apparatus according to claim 7 wherein said rubberized lining is adhered to the interior surface of said metal bowl.

9. The sharps destruct apparatus according to claim 6 wherein said magnet attached is said metal bowl is removable from said metal bowl.

10. The sharps destruct apparatus according to claim 6 wherein said magnet attached to said metal bowl is swivelly attached to said metal bowl.

11. The sharps destruct apparatus according to claim 2 further including means for periodically vibrating said cathode to dislodge deposits on said cathode.

12. The sharps destruct apparatus according to claim 2 further including means for sanitizing liquids in said chamber.

13. The sharps destruct apparatus according to claim 12 wherein said means for sanitizing includes means for introducing ozone into said chamber.

14. The sharps destruct apparatus according to claim 12 wherein said means for sanitizing includes the introduction of a blend of detergent and germicide.

15. The sharps destruct apparatus according to claim 1 further including means for heating and sharps upon insertion into said opening.

16. The sharps destruct apparatus according to claim 15 wherein said opening is slotted.

17. A sharps disposal system comprising:
a) a chamber for receipt of said sharps;
b) an electrolytic solution contained in said chamber;
c) an anode positioned along an interior portion of a first wall of said chamber;
d) a cathode positioned along an interior portion of a second wall of said chamber;
e) a door mechanism;
f) a proximity sensor for opening said door mechanism when an object is within a selected zone of said door mechanism; and, g) means for supplying electrical current between said anode and said cathode via said electrolytic solution such that metallic sharps are dissolved in said electrolytic solution.

18. The sharps disposal system according to claim 17 further including a magnet positioned along an exterior portion of said first wall for holding sharps proximate to said anode.

19. The sharps disposal system according to claim 18 further including:
   a) an opening located in a top portion of the chamber for receipt of said sharps;
   b) means for withdrawing said sharps from a handle portion when said sharps are inserted through said opening; and,
   c) means for depositing withdrawn sharps in said chamber.

20. The sharps disposal system according to claim 19 further including means for heating said sharps upon insertion into said opening.

21. The sharps disposal system according to claim 20 wherein said opening is slotted.

22. The sharps disposal system according to claim 18 further including means for periodically vibrating said cathode to dislodge deposits on said cathode.

23. The sharps disposal system according to claim 22 further including means for flushing liquid materials containing said dissolved metallic sharps from said chamber.

24. The sharps disposal system according to claim 18 further including means for sanitizing liquids in said chamber.

25. The sharps disposal system according to claim 24 wherein said means for sanitizing includes means for introducing ozone into said chamber.

26. The sharps disposal system according to claim 24 wherein said means for sanitizing includes the introduction of a blend of detergent and germicide.

27. The sharps disposal system according to claim 17 further including a proximity sensor for opening said door mechanism means when an object is within a selected zone of said door mechanism means.

28. The sharps disposal system according to claim 27 further including a container means for holding said sharps prior to introduction into said chamber.

29. The sharps disposal system according to claim 28 wherein said container means includes:
   a) a metal bowl; and,
   b) a magnet attached to an exterior portion of said metal bowl.

30. The sharps disposal system according to claim 29 further including a rubberized lining on an interior surface of said metal bowl.

31. The sharps disposal system according to claim 30 wherein said rubberized lining is adhered to the interior surface of said metal bowl.

32. The sharps disposal system according to claim 29 wherein said magnet is removable from said metal bowl.

33. The sharps disposal system according to claim 29 wherein said magnet is swivelly attached to said metal bowl.

34. A sharps disposal system comprising:
   a) a container means for holding said sharps prior to disposal, said container means having,
      1) a metal bowl, and,
      2) a magnet attached to an exterior portion of said metal bowl; and
   b) a disposal mechanism having,
      1) an enclosed chamber,
      2) an electrolytic solution contained in said chamber,
      3) an anode positioned along an interior portion of a first wall of said chamber,
      4) a cathode positioned along an interior portion of a second wall of said chamber,
      5) a magnet positioned along an exterior portion of said first wall for holding sharps proximate to said anode,
      6) means for supplying electrical current between said anode and said cathode via said electrolytic solution such that said sharps are dissolved into said electrolytic solution,
      7) an opening in a top portion of said enclosed chamber for receipt of said sharps from said container means; and,
      8) means for discharging said electrolytic solution with dissolved sharps.

35. The sharps disposal system according to claim 34 wherein said opening includes a door mechanism means for covering said opening when said apparatus is not in use.

36. The sharps disposal system according to claim 35 further including a proximity sensor for opening said door mechanism means when an object is within a selected zone of said door mechanism means.

37. The sharps disposal system according to claim 36 further including a rubberized lining on an interior surface of said metal bowl.

38. The sharps disposal system according to claim 37 wherein said rubberized lining is adhered to the interior surface of said metal bowl.

39. The sharps disposal system according to claim 38 wherein said magnet attached to said metal bowl is removable from said metal bowl.

40. The sharps disposal system according to claim 38 wherein said magnet attached is said metal blow is swivelly attached to said metal bowl.

41. The sharps disposal system according to claim 36 further including:
   a) means for withdrawing said sharps from a handle portion when said sharps are inserted through said opening; and,
   b) means for depositing withdrawn sharps in said chamber.

42. The sharps disposal system according to claim 41 further including means for heating said sharps upon insertion into said opening.

43. The sharps disposal system according to claim 42 wherein said opening is slotted.

44. The sharps disposal system according to claim 36 further including means for periodically vibrating said cathode to dislodge deposits on said chamber.

* * * * *